US 6,771,566 B2

(12) United States Patent
Lee

(10) Patent No.: US 6,771,566 B2
(45) Date of Patent: Aug. 3, 2004

(54) WRISTWATCH EQUIPPED WITH DEVICE FOR ELIMINATION OF STATIC ELECTRICITY

(76) Inventor: Bok-Kwon Lee, 362-101, Jigok Green Villa, Jigok-dong, Nam-gu, Pohang-si, Gyeongsangbuk-do (KR), 790-751

( * ) Notice: Subject to any disclaimer, the term of this patent is extended or adjusted under 35 U.S.C. 154(b) by 0 days.

(21) Appl. No.: 10/367,171

(22) Filed: Feb. 14, 2003

(65) Prior Publication Data

US 2004/0008583 A1 Jan. 15, 2004

(30) Foreign Application Priority Data

Jul. 15, 2002 (KR) .......................... 20-2002-0021501 U

(51) Int. Cl.[7] .................... G04B 47/00; G04B 37/00; G04B 19/00; G04C 17/00; H02H 1/00
(52) U.S. Cl. ......................... 368/10; 368/11; 368/69; 368/224; 368/88; 368/286; 361/212; 361/220
(58) Field of Search ...................... 368/10, 11, 69, 368/88, 224, 286, 204, 293

(56) References Cited

U.S. PATENT DOCUMENTS

| 4,478,524 A | * | 10/1984 | Saitoh et al. ............... 368/204 |
| 4,638,399 A | * | 1/1987 | Maroney et al. ............ 361/220 |
| 4,639,825 A | * | 1/1987 | Breidegam .................. 361/212 |
| 4,711,584 A | * | 12/1987 | Tanazawa et al. ............ 368/88 |
| 4,737,941 A | * | 4/1988 | Kamiyama et al. ........... 368/77 |
| 5,457,596 A | * | 10/1995 | Yang .......................... 361/220 |
| 5,461,369 A | * | 10/1995 | Campbell et al. ........... 340/649 |
| 6,150,945 A | * | 11/2000 | Wilson ....................... 340/661 |
| 6,521,822 B2 | * | 2/2003 | Ito et al. ..................... 136/244 |

FOREIGN PATENT DOCUMENTS

JP     35414326 A   *   11/1979  ................. 368/286

* cited by examiner

Primary Examiner—David Martin
Assistant Examiner—Michael L. Lindinger
(74) Attorney, Agent, or Firm—Dilworth & Barrese, LLP

(57) ABSTRACT

Disclosed herein is a wristwatch equipped with a device for the elimination of static electricity, the static electricity resulting from contact with metallic wardrobes, textiles, automobiles, electronic devices, and so on. Ground protrusions are disposed on a metallic upper cover in the upper portion of the watch. An external casing through which electricity is not transmitted is disposed in the middle portion of the watch. Connection protrusions and a watch chain are disposed in the lower portion of the watch. The device along with components of a general wristwatch is disposed in the watch, includes a coil for preventing a rapid current surge, a resistor for performing discharge, and a discharge bulb connected in series with each other, and is connected from the upper cover to one of the connection protrusions. Accordingly, static electricity is eliminated by touching objects generating the static electricity to ground protrusions disposed on the upper cover.

7 Claims, 1 Drawing Sheet

WRISTWATCH EQUIPPED WITH DEVICE FOR ELIMINATION OF STATIC ELECTRICITY

This application claims priority to an application entitled "WRISTWATCH EQUIPPED WITH DEVICE FOR ELIMINATION OF STATIC ELECTRICITY", filed in the Korean Intellectual Property Office on Jul. 15, 2002 and assigned Serial No. 2002-21501, the contents of which is incorporated herein by reference.

BACKGROUND OF THE INVENTION

1. Field of the Invention

The present invention relates generally to a wristwatch equipped with a device for the elimination of static electricity.

2. Description of the Prior Art

When people touch metallic chests, textiles, automobiles, electronic devices and so on in their daily live, the discharge of static electricity occurs often, so people are startled and irritated.

Further, the discharge of static electricity has a bad effect on the health of people.

One of parts where the discharge of static electricity occurs quite often is a part of the human body which touches objects, such as the wrist, the forearm and so on. Accordingly, if devices for preventing static electricity are installed in wristwatches worn on wrists, the static electricity may be effectively eliminated.

An object of the present invention is to provide a wristwatch equipped with a device for the effective elimination of static electricity, which includes a wristwatch having a certain construction, a coil, a resistor, and a discharge bulb connected in series with each other.

There have been used various types of apparatuses for eliminating static electricity from the human body.

For example, there have been used automobile keys with apparatuses for the elimination of static electricity installed therein, key rings having function for the elimination of static electricity, and apparatuses for the elimination of static electricity installed in footwear.

Conventional apparatuses for the elimination of static electricity, such as automobile keys with apparatuses for the elimination of static electricity installed therein or key rings having function for the elimination of static electricity, are disadvantageous in that it is inconvenient for people to touch bodies of the apparatuses after taking the apparatuses carried in their purses and so on out of the purses and holding the apparatuses in their hands. Conventional apparatuses for the elimination of static electricity, such as apparatuses for the elimination of static electricity installed in footwear, are disadvantageous problematic in that they cannot be used at places where footwear is taken off. Additionally, the conventional apparatuses for the elimination of static electricity have individual constructions regardless of general wristwatches.

SUMMARY OF THE INVENTION

Accordingly, the present invention has been made keeping in mind the above problems occurring in the prior art, and an object of the present invention is to provide a wristwatch equipped with a device for the elimination of static electricity, which has a significantly simple construction and can maximize the effect of the elimination of) static electricity.

That is, the device for the elimination of static electricity is installed in a wristwatch, and objects are contacted by the ground protrusions of the device that are disposed on an upper cover of the wristwatch worn on the wrist of a user without holding the device in his hand, thereby conveniently eliminating static electricity affecting the human body, and eliminating static electricity using the wristwatch regardless of places.

In order to accomplish the above object, the present invention provides a wristwatch, comprising a watch body, and a device for the elimination of static electricity, wherein the watch body is equipped with the device for the elimination of static electricity.

Preferably, the device for the elimination of static electricity includes a coil, a resistor, and a discharge bulb connected in series with each other by conducting wires.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
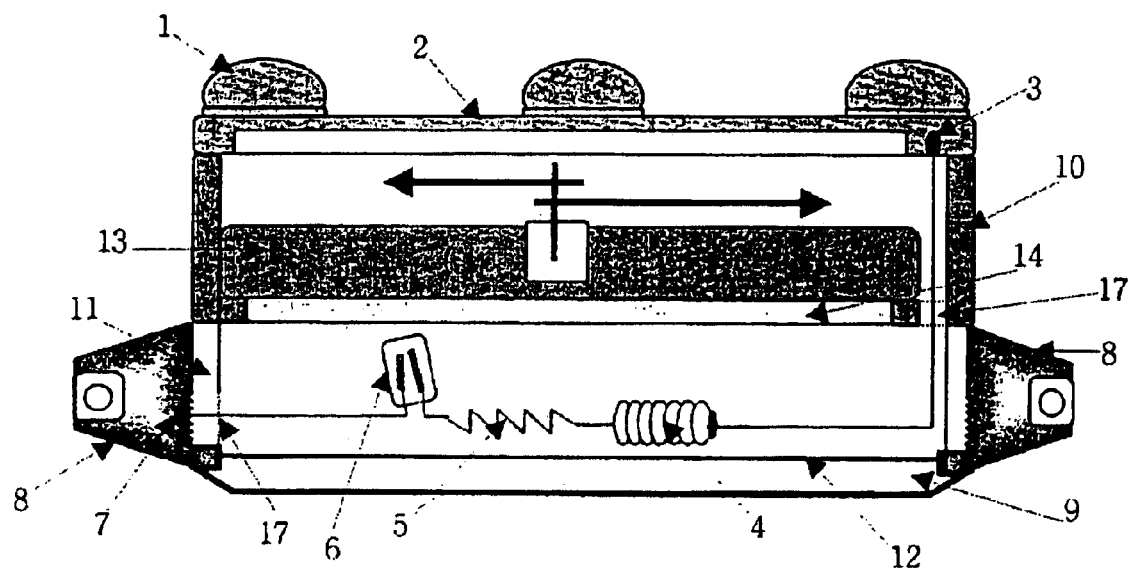
FIG. 1 is a sectional view of a wristwatch equipped with a device for the elimination of static electricity in accordance with the present invention.

Reference now should be made to the drawings, in which the same reference numerals are used throughout the different drawings to designate the same or similar components.

Figure 2:
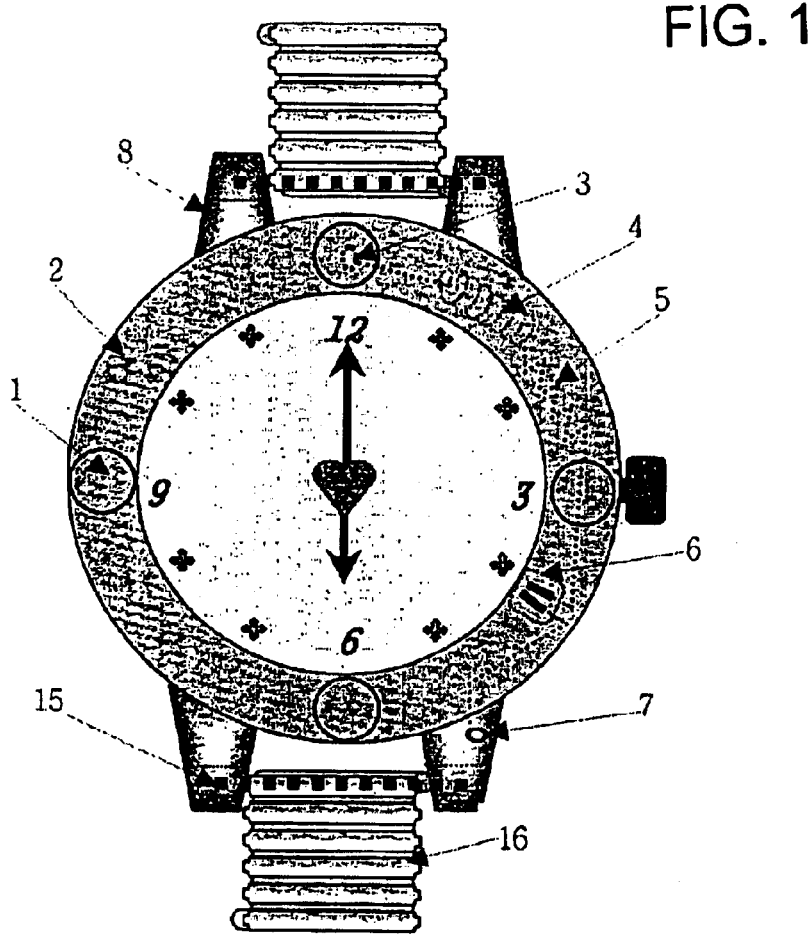
FIG. 2 is a plan view of the wristwatch equipped with the device for the elimination of static electricity in accordance with the present invention.

FIG. 1 is a sectional view of a wristwatch equipped with a device for the elimination of static electricity in accordance with the present invention. FIG. 2 is a plan view of the wristwatch equipped with the device for the elimination of static electricity in accordance with the present invention.

As shown in FIGS. 1 and 2, the wristwatch includes a lower cover 9, an external casing 10, an upper cover 2, and the device for the elimination of static electricity. A partition wall 14 made of synthetic resin is positioned inside the wristwatch and is detachably attached to the external casing 10 made,of synthetic resin. The lower cover 9 made of a conductive metallic material is detachably disposed under the external casing 10. Components 13 of a general wristwatch are disposed on the partition wall 14 inside the wristwatch. The upper cover 2 made of a metallic material is formed in the shape of a ring on the external casing 10. A transparent plate is disposed in the upper cover 2 to be fitted into the inner circumference of the ring. Ground protrusions 1 made of metallic materials are formed on the ring at predetermined intervals of the upper cover 2. Two pairs of connection protrusions 8 are formed at both sides of lower portions of the external casing 10, respectively. The connection protrusions 8 are disposed at predetermined intervals, and are electrically coupled to the lower cover 9. Both ends of a watch chain 16 made of a metallic material are electrically connected to two pairs of the connection protrusions 8 through metallic connection pins 15, respectively. The device for the elimination of static electricity is disposed in a space between the partition wall 14 and the lower cover 9. One terminal of the circuit of the device for the elimination of static electricity is electrically connected through a through hole 17 to a first connection 7 disposed in one of the connection protrusions 8. The other terminal of the circuit of the device for the elimination of static electricity is electrically connected through a through hole 17 to a second connection 3 disposed inside the upper cover 2.

In this case, the device for the elimination of static electricity includes a discharge bulb 6, a resistor 5, and a coil 4. The discharge bulb 6 is electrically connected to the first connection 7. The resistor 5 is electrically connected in series to the discharge bulb 6. The coil 4 electrically connected to the second connection 3 is electrically connected in series to the resistor 5 by a conducting wire.

Further, it is preferable that the external casing 10 is made of synthetic resin so that electricity is not transmitted between the upper cover 2 and the lower cover 9. Further, it is preferable that a transparent casing 11 made of a transparent material is disposed in the lower part of the external casing 10 so that the lighting state of the discharge bulb 6 may be observed.

With this construction, electricity, which flows from the human body through the watch chain 16 in contact with the wrist of a user wearing the wristwatch, flows to the discharge bulb 5 and the resistor 6 via the connection pins 15, connection protrusions 8 and the first connection 7, and is discharged. Further, static electricity generated from the outside is transmitted to one or more of the ground protrusions 1 of the upper cover 2, flows through the resistor 5 and the discharge bulb 6 through the second connection 3, and is discharged.

At this time, the coil 4 temporarily stores a small or large amount of current inputted through one or more of the ground protrusions 1 and performs a buffering function. Further, the discharge bulb 6 is lighted, so lighting can be observed through the transparent casing 11.

It is preferable that the ground protrusions 1 are made of metallic materials having a convex shape so that objects are easily contacted by the ground protrusions 1 and electricity is easily transmitted through the ground protrusions 1. It is preferable that an insulating material 12 is disposed on the inner surface of the lower cover 9 to insulate the device for eliminating static electricity from the lower cover 9.

As described above, the present invention provides a wristwatch equipped with a device for the elimination of static electricity, in which static electricity resulting from contact with automobiles, electronic devices, various textiles, or metallic materials and being accumulated in the objects is transmitted to the device for the elimination of static electricity through the ground protrusions formed on the upper cover of the wristwatch, and is discharged through the resistor and the discharge bulb, thereby minimizing shock by the static electricity and annoyance due to the shock. Further, the present invention provides a wristwatch equipped with a device for the elimination of static electricity, in which a function of eliminating static electricity is integrated into a wristwatch usually worn in a wrist of a user, thereby facilitating the carrying and use of the wristwatch and effectively reducing shock by static electricity generated in the case where a user dresses or undresses.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A wristwatch, comprising:

a watch body; and a device for the elimination of static electricity;

wherein the watch body is equipped with the device for the elimination of static electricity including an electric charge accumulator, a resistor, and a discharge bulb connected in series with each other by conducting wires.

2. The wristwatch according to claim 1, wherein:

the watch body comprises an upper cover made of a metallic material to transmit electricity, a lower cover made of a metallic material to transmit electricity, and an external casing made of synthetic resin to insulate the upper and lower covers from each other; and the device for the elimination of static electricity is connected to the upper and lower covers.

3. The wristwatch according to claim 2, further comprising a plurality of ground protrusions formed on the upper cover.

4. The wristwatch according to claim 3, further comprising a watch chain made of a metallic material and attached to the watch body.

5. The wristwatch according to claim 2, further comprising a casing made of a transparent material and disposed in a lower part of the external casing to observe a lighting state of the discharge bulb.

6. A wristwatch, comprising:

a watch body; and a device for the elimination of static electricity including an electric discharge indicator mounted within and connected across the watch body.

7. The wristwatch according to claim 6, wherein the the electric discharge indicator includes an electric charge accumulator, a resistor, and a discharge bulb connected in series with each other by conducting wires.

* * * * *